(12) United States Patent
Bublick et al.

(10) Patent No.: US 9,295,579 B1
(45) Date of Patent: Mar. 29, 2016

(54) CUFF AND CUFF/CONDOM COMBINATION FOR ERECTION ASSISTANCE

(71) Applicants: Ronald G Bublick, Virginia Beach, CA (US); Linda L Bublick, Virginia Beach, CA (US)

(72) Inventors: Ronald G Bublick, Virginia Beach, CA (US); Linda L Bublick, Virginia Beach, CA (US)

(73) Assignee: ENCORE PRODUCTS INC, Virginia Beach, VA (US)

( * ) Notice: Subject to any disclaimer, the term of this patent is extended or adjusted under 35 U.S.C. 154(b) by 0 days.

(21) Appl. No.: 14/824,650

(22) Filed: Aug. 12, 2015

(51) Int. Cl.
*A61F 5/00* (2006.01)
*A61F 5/41* (2006.01)
*A61F 6/04* (2006.01)

(52) U.S. Cl.
CPC ... *A61F 5/41* (2013.01); *A61F 6/04* (2013.01); *A61F 2005/411* (2013.01); *A61F 2005/414* (2013.01)

(58) Field of Classification Search
CPC ............. A61F 5/41; A61F 6/02; A61F 6/04
USPC ............................. 600/38–41; 128/842–844
See application file for complete search history.

(56) References Cited

U.S. PATENT DOCUMENTS

| 5,509,891 | A * | 4/1996 | DeRidder | A61F 5/05841 |
| | | | | 600/38 |
| 5,622,186 | A * | 4/1997 | Schwartz | A61F 5/41 |
| | | | | 128/842 |
| 6,776,755 | B1 * | 8/2004 | Raskin | A61F 5/41 |
| | | | | 600/39 |
| 2006/0048784 | A1 * | 3/2006 | Turner | A61F 6/04 |
| | | | | 128/844 |
| 2007/0144529 | A1 * | 6/2007 | Bryant | A61F 6/04 |
| | | | | 128/844 |

* cited by examiner

*Primary Examiner* — John Lacyk
(74) *Attorney, Agent, or Firm* — Peter J. Van Bergen

(57) ABSTRACT

A device providing erection assistance includes a first sleeve of flaccid material that can fit over a male penis and extend from the base to the corona of the penis. Also included is a second sleeve of flaccid material of similar length that can fit over the penis. One or more wall regions are disposed between the first and second sleeves. The wall region(s) extend(s) continuously along the lengths of the first and second sleeves. The wall region(s) is (are) coupled to the first and second sleeves, and define a void region along the length of the sleeves that is readily aligned with the urethral tube of a male user.

26 Claims, 4 Drawing Sheets

US 9,295,579 B1

CUFF AND CUFF/CONDOM COMBINATION FOR ERECTION ASSISTANCE

FIELD OF THE INVENTION

The invention relates generally to non-surgical-based sexual aids, and more particularly to cuffs and cuff/condom combinations that provide erection assistance when worn by a man.

BACKGROUND OF THE INVENTION

Options for males experiencing erectile dysfunction (or "ED" as it is also known) include worn devices, surgically-implanted devices, external equipment, and ingested medications. Surgically-implanted devices, external equipment, and ingested medications are expensive, and can present a variety of post-use health risks and/or potential side effects. Worn devices generally avoid the expense and health risks associated with implanted devices and medications. However, existing worn devices have not been effective thereby leaving ED-afflicted males with no solution other than reliance on the more expensive and riskier surgically-implanted devices and ingested medications.

SUMMARY OF THE INVENTION

Accordingly, it is an object of the present invention to provide a device for use by a male to improve his sexual experience.

Another object of the present invention is to provide a simple and effective device that can be worn by a male experiencing erectile dysfunction in order to provide erection assistance.

Still another object of the present invention is to provide a device that can be used by a male as a non-surgical-based, non-medicinal aid for erectile dysfunction that presents no health risks to the male or his partner.

Other objects and advantages of the present invention will become more obvious hereinafter in the specification and drawings.

In accordance with the present invention, a device providing erection assistance includes a first sleeve of flaccid material adapted to fit over a male penis and having a length extending from the base of the penis to at least the corona of the penis. Also included is a second sleeve of flaccid material adapted to fit over the penis and having a length extending from the base of the penis to at least the corona of the penis. At least one wall region is disposed between the first sleeve and second sleeve. The wall region(s) extends continuously along the lengths of the first sleeve and second sleeve. The wall region(s) is (are) coupled to the first sleeve and second sleeve. The wall region(s) define a void region along the length of the first sleeve and second sleeve that is readily aligned with the urethral tube of a male user.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
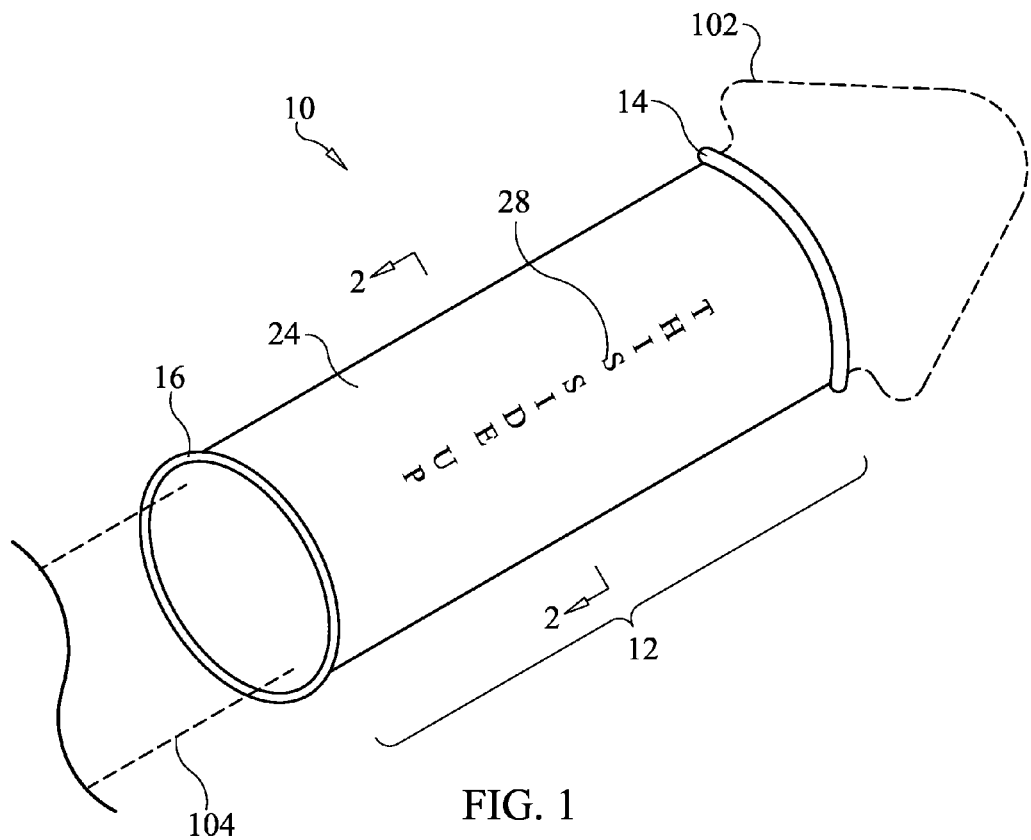
FIG. 1 is a perspective view of a cuff that can be worn by a male in accordance with an embodiment of the present invention.
Figure 2:
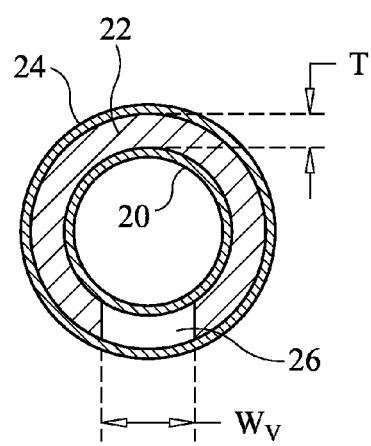
FIG. 2 is a cross-sectional view taken along line 2-2 in FIG. 1.

Referring now to the drawings, simultaneous reference will be made to FIGS. 1 and 2 where a cuff for use as a non-surgical-based and non-medicinal device that provides erection assistance for a male is shown and is referenced generally by numeral 10. Cuff 10 can be used by a male experiencing erectile dysfunction (or "ED"), or by a male seeking a firmer and/or longer-lasting erection. Cuff 10 is generally an open-ended tube having a tubular body 12 terminating at either end thereof in bands or rings 14 and 16. Rings 14 and 16 can be similar to the rolled ring formed at the opening of conventional condoms. Rings 14 and 16 are coupled to tubular body 12.

In general, cuff 10 is placed on/over a partially erect or even flaccid male penis to thereby provide erection assistance to the wearer. As used herein, the term "erection assistance" means that cuff 10 in combination with a flaccid or partially erect penis provides a shape whose firmness is sufficient to support sexual intercourse. In terms of length, cuff 10 is sized to fit just behind the corona or glans 102 (i.e., the ridge around the base of the head of the penis) of a penis (shown in dashed lines), and extend to the base 104 of the penis such that the penis length to include cuff 10 is extended to the range of a typically erect penis. Materials used for cuff 10 can include, but are not limited to, materials used in the manufacture of condoms to include latex/natural rubber, all forms of synthetic rubber, polyester, polyethylene, plastics, lambskin, and combinations thereof. Cuff 10 can be constructed to stretch outward in the radial direction such that it applies inward radial pressure when used. Cuff 10 could be made in one size, several general sizes, or could be specially sized such that its diameter is adapted for a specific user.

Tubular body 12 is a three-layer structure defined by an open-ended sleeve or tubular lining 20 extending the length of tubular body 12, a wall region 22 extending the length of tubular body 12, and an open-ended sleeve or tubular covering 24 extending the length of tubular body 12. Each of lining 20 and covering 24 is made from a thin, flaccid material having material and dimensional attributes generally similar to those used in the manufacture of conventional condoms. For example, the thickness of lining 20 and covering 24 will generally be in the range of approximately 0.03 millimeters (mm) to approximately 0.09 mm. It is to be understood that the thicknesses of lining 20 and covering 24 relative to that of wall region 22 have been exaggerated in the drawings for clarity of illustration. Lining 20 and covering 24 are coupled to the inside radial surface and outside radial surface, respectively, of wall region 22. Lining 20 and covering 24 are coupled to each other at opposing axial ends of tubular body 12.

Wall region 22 is a solid wall structure that is substantially tubular except for a gap or void 26 defined all along the length of wall region 22. That is, wall region 22 is a longitudinally-split, solid-wall, hollow cylinder. Wall region 22 can also be made using materials typically used in the manufacture of condoms. However, the thickness "T" of wall region 22 defines a structure that, when held in a horizontal orientation from one axial end thereof, substantially maintains the horizontal orientation. For example, when wall region 22 is made using a condom-type of latex material, the thickness T of wall region 22 can be in the range of approximately 0.1 inches to approximately 0.25 inches to satisfy the horizontal orientation maintenance requirement. For comfort as well as manufacturing and cost considerations, it is preferred to keep thickness T to a minimum while still retaining the horizontal maintenance requirement noted above. In the illustrated embodiment, thickness T is constant all along the length of wall region 22.

In use, the gap or void 26 defined by wall region 22 is to be aligned with the wearer's urethral tube that runs along the length of the underside of the penis. When aligned with the wearer's urethral tube, void 26 defines a region of cuff 10 along which little to no radial pressure will be applied to the wearer's penis. The width $W_V$ of void 26 can be in the range of approximately 0.25 inches to approximately 0.4 inches to provide spacing that accommodates slight misalignment and anatomical differences between users while still maintaining the above-described horizontal orientation requirement. To provide alignment guidance, tubular body 12 can have visual and/or tactile indicia to assist with alignment of cuff 10. For example, the illustrated embodiment's indicia includes verbiage 28 (as shown) indicating the top of cuff 10 (as viewed when worn). Verbiage 28 is located in diametric opposition to void 26 to facilitate alignment of void 26 with the wearer's urethral tube. Verbiage 28 can be printed letters, and/or can be formed by raised letters, shapes, etc., to provide a tactile indicator for proper alignment. Verbiage 28 (and/or tactile indicia) can be provided on covering 24 and/or the portion of wall region 22 in contact with covering 24. The stiffness or rigidity of cuff 10 provides erection assistance to a flaccid or partially erect penis, while void 26 provides for unimpeded semen or urine flow through the urethral tube.

As mentioned above, tubular body 12 terminates at its opposing axial ends in bands or rings 14 and 16. Each of rings 14 and 16 is generally elastic and sized to snugly fit on a penis to hold cuff 10 in place and without slipping on the penis. Rings 14 and 16 can be made from the same or different materials and/or colors as tubular body 12 without departing from the scope of the present invention. Rings 14 and 16 can be integrally formed with tubular body 12. For example, rings 14 and 16 could be positioned/captured between the layers of tubular body 12, or could be integrated with lining 20 and/or covering 24. Each of rings 14 and 16 could be formed by a rolled amount of the material used for lining 20 or covering 24 similar to the rolled ring end of a conventional condom. Once placed on a flaccid penis, cuff 10 provides extension (via the length of cuff 10) and axial rigidity forces to the penis such that the combination of the penis and cuff 10 presents a structure suitable for sexual intercourse. As will be explained further below, rings 14 and 16 could also provide radial pressure in a way that promotes or maintains an erection. Ring 14 and/or ring 16 (and/or tubular body 12) could also have vibrating device(s)/element(s) coupled thereto without departing from the scope of the present invention. One or more additional rings could be provided at interim position(s) along tubular body 12 where such additional ring(s) can be integrally formed with tubular body 12 or manually placed thereon without departing from the scope of the present invention.

Figure 3:
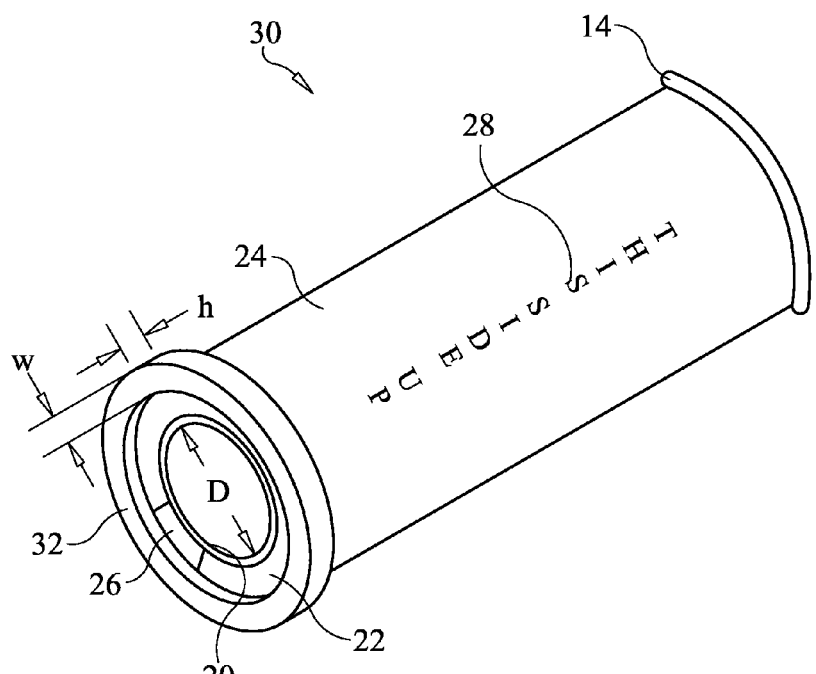
FIG. 3 is a perspective view of a cuff having a solid base ring in accordance with another embodiment of the present invention.

The forces applied by cuff 10 can be achieved and/or enhanced in a variety of ways without departing from the scope of the present invention. For example, FIG. 3 illustrates another cuff embodiment of the present invention that is referenced generally by numeral 30. In this embodiment, cuff 30 is similar to cuff 10 described above, but replaces ring 16 with a solid base ring 32 made from a material used in the manufacture of condoms. In general, the height ("h") and width ("w") dimensions of base ring 32 are several times that of a ring 16 having the dimensions of a rolled ring at the open end of a conventional condom. For example, when using a condom-type of latex material for base ring 32, the height h and width w dimensions for base ring 32 are each in the range of approximately 0.1 inches to approximately 0.3 inches, while the inner diameter "D" of base ring 32 should form a snug fit with the base of a penis. In this way, base ring 32 will still be able to stretch elastically to fit onto a penis, but its increased height/width dimensions will also apply a greater amount of inward radial pressure to the base of a penis as compared to a conventional condom's rolled ring.

Figure 4:
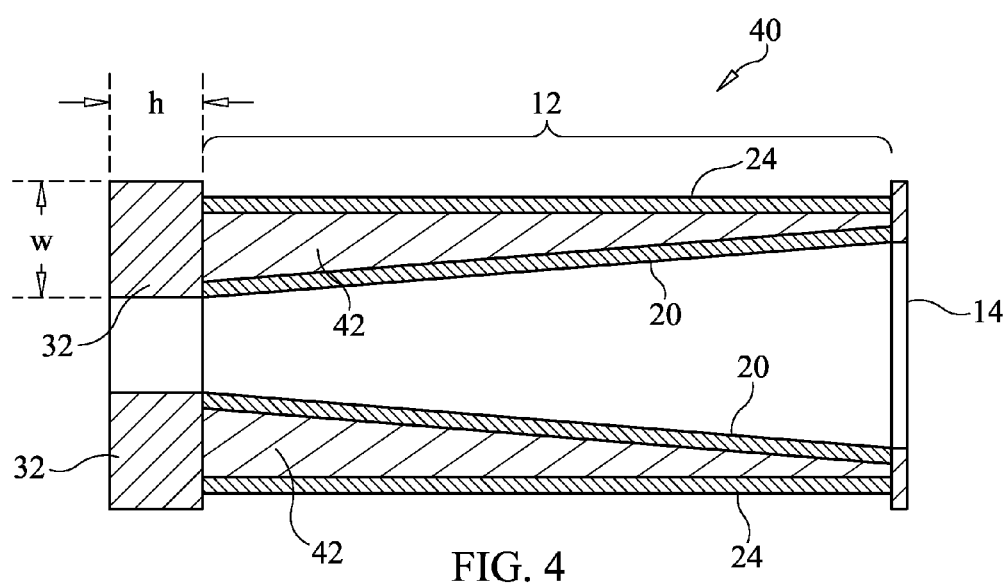
FIG. 4 is an axial cross-sectional view of a cuff whose wall region's thickness varies as a function of axial location in accordance with another embodiment of the present invention.

The thickness of wall region 22 can be the same along its length (as is the case in the embodiments illustrated in FIGS. 1-3), or could be varied along its length without departing from the scope of the present invention. For example, FIG. 4 illustrates another cuff 40 similar to cuff 30, but whose tubular body 12 has a wall region 42 whose thickness varies along its length with the wall region being thicker at or toward one end (e.g., near base ring 32) than at its other end (e.g., near ring 14). In this way, a user could place the thicker-wall and more rigid portion of tubular body 12 near base ring 32 at the base of his penis so that the thinner-wall portion of tubular body 12 is adjacent the glans of the penis to maintain comfort and sensitivity. It is to be understood that the scale of varying-thickness wall region 42 has been exaggerated for purposes of illustration.

The present invention is not limited to the use of a single wall region between lining 20 and covering 24. That is, the cuff of the present invention could also use multiple, spaced-apart solid-wall regions or strips (as they will be referred to hereinafter) of material. In general, such solid strips take the place of the above-described wall region. While each individual strip does not provide a substantial amount of horizontal rigidity, the combination of multiple, spaced-apart solid strips coupled to lining 20 and covering 24 define a multiple-beam structure having a greater horizontal orientation maintenance or rigidity than any single element thereof.

Figure 5:
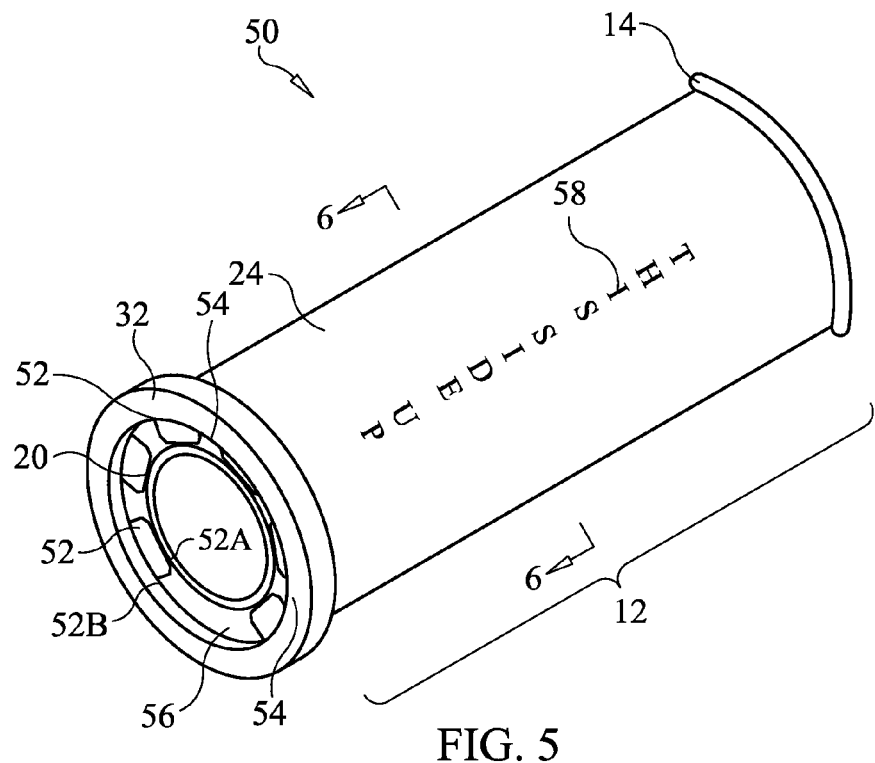
FIG. 5 is a perspective view of a cuff that includes multiple, spaced-apart wall regions or strips in accordance with another embodiment of the present invention.
Figure 6:
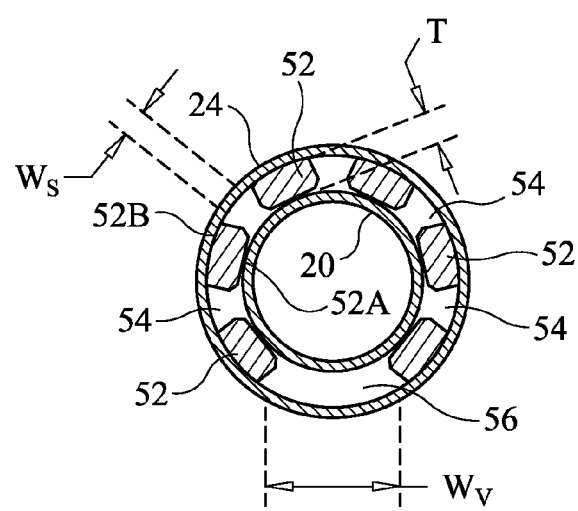
FIG. 6 is a cross-sectional view taken along line 6-6 in FIG. 5.
Figure 7:
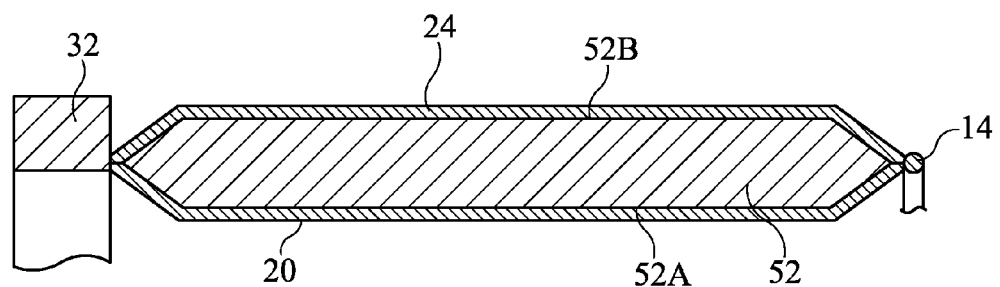
FIG. 7 is a longitudinal cross-section of a single wall region/strip coupled to the inner lining and outer covering in accordance with an embodiment of the present invention.

By way of example, FIGS. 5 and 6 illustrate a cuff 50 having a plurality of axially-extending and spaced-apart strips 52 incorporated into tubular body 12. As in the previous embodiments, lining 20 and covering 24 are coupled to each of strips 52. At a minimum, lining 20 is coupled to each radially-inward face 52A of each strip 52, and covering 24 is coupled to each radially-outward face 52B of each strip 52. Lining 20 and covering 24 can be coupled to each other or uncoupled from each other in each longitudinal space 54 defined between adjacent strips 52 without departing from the scope of the present invention. Each of strips 52 extends substantially along the length of tubular body 12. Each of strips 52 can be made from the same or different material used for lining 20 and covering 24. Strips 52 can all be the same size. However, different sizes of strips 52 could be used to enhance extension/rigidity forces without departing from the scope of the present invention. When using a condom-type of latex material for strips 52, the thickness T of each strip 52 can be in the range of approximately 0.1 inches to approximately 0.25 inches. The cross-sectional shape of strips 52 can be round, oblong, triangular, square, etc., and is not a limitation of the present invention. In the illustrated example, each of strips 52 is generally rectangular with its corners that are adjacent to lining 20 being rounded or chamfered for user comfort. The opposing longitudinal ends of each strip 52 can be tapered (or rounded) for user comfort as illustrated in FIG. 7 where a single strip 52 is illustrated in a longitudinal cross-section thereof with lining 20 and covering 24 coupled to faces 52A and 52B, respectively, as described above. Similar to previously-described embodiments, lining 20 and covering 24 are coupled to ring 14 and base ring 32.

As with the previous embodiments, a gap or void 56 is defined along tubular body 12 and indicia 58 are provided on tubular body 12 in diametric opposition to void 56. Void 56 is analogous in size and function to void 26 described earlier herein. Spaced-apart strips 52 can be provided in an even distribution about the tubular body on either side of void 56, or in a varied distribution, without departing from the scope of the present invention. In general, the width $W_S$ of each longitudinal space 54 is less than the width $W_V$ of void 56. By way of a non-limiting illustrative example, for strips 52 that are approximately 0.25 inches wide, the width $W_S$ can be approximately 0.125 inches. The width $W_V$ of void 56 can be in the range of approximately 0.25 inches to approximately 0.4 inches.

Figure 8:
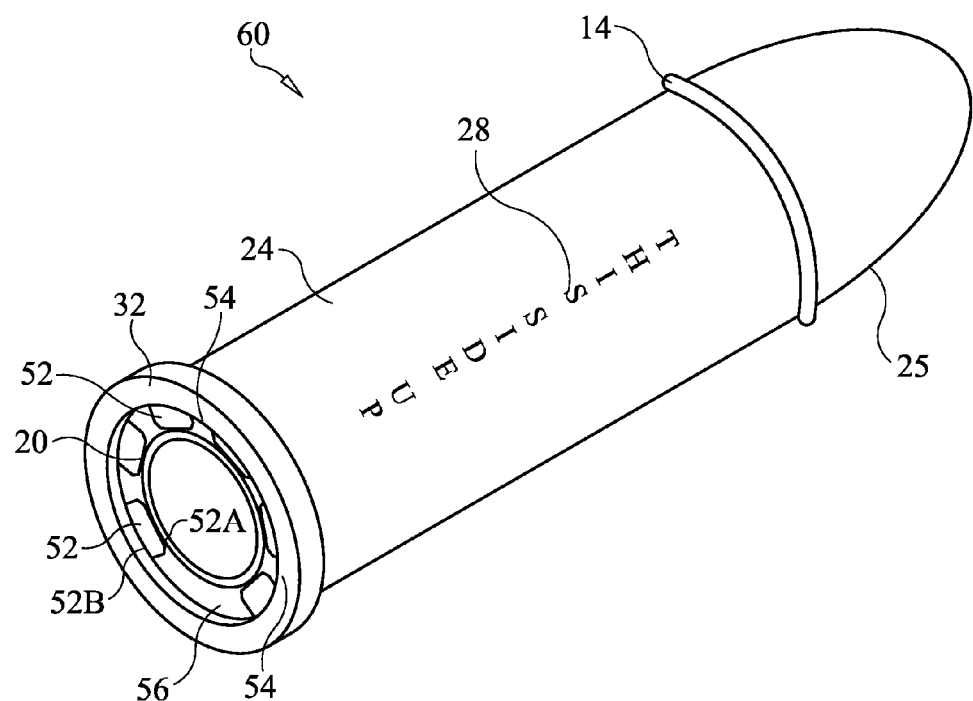
FIG. 8 is a perspective view of a cuff and condom combination in accordance with an embodiment of the present invention.

The cuff of the present invention can also be incorporated into a condom. For example, FIG. 8 illustrates a cuff/condom combination referenced generally by numeral 60. Cuff/condom 60 is based on the previously-described cuff 50. However, it is to be understood that each of the above-described cuff embodiments (or permutations thereof) could form the basis of a cuff/condom combination without departing from the scope of the present invention. In cuff/condom 60, covering 24 extends beyond ring 14 to define a closed end sheath 25 such that covering 24 and closed end sheath 25 combine to define a condom. Additionally or alternatively, lining 20 could be similarly extended to define the closed end sheath of a condom. Ring 14 can be on the inside of cuff/condom 60 (e.g., part of lining 20), or on the outside of cuff/condom 60 (e.g., part of covering 24 as shown) without departing from the scope of the present invention.

The extension and axial rigidity forces provided by the present invention can be the primary cause of an erect structure defined by a male's penis in combination with one of the present invention's cuff or cuff/condom. In addition, the present invention non-invasively aids the natural erection process by directing or encouraging blood flow into a penis to help start an erection, and/or impeding blood flow from the penis as and after a partial or full erection has started or been achieved. The present invention non-invasively assists the holding of more blood in a penis than is allowed to flow out to thereby aid in the maintenance of an erection. Such encouragement and/or prevention of blood flow are assisted by the above-described base ring and tubular body. For example, the present invention's wall region(s) and/or solid base ring press upon the Corpora Cavernosa (located in the penile shaft or cuffed-wall areas of the penis) as well as the myriad penile veins and arteries to cause greater amounts of blood to collect in the penis. The side-by-side paired Corpora Cavernosa include sensitive erectile tissue that are affected by the inward radial pressure caused by the wall region(s) and base ring. The wall region(s) apply pressure to the outside of the penis that, in turn, is transferred to the Corpora Cavernosa to direct, encourage, or impede the flow of blood into or out of veins and arteries in the penis. Thus, in general, the devices described herein apply pressure to the outside of the penis to direct, encourage, or impede the flow of blood into or out of penile veins and arteries for purpose of retaining sufficient blood in a penis to provide erection assistance.

The advantages of the present invention are numerous. The cuff and cuff/condom combination are simple and inexpensive devices that can be used when needed or desired to provide erection assistance. Use of each device requires no surgical implantation and has no medical side effects.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A device providing erection assistance, comprising:
   a first sleeve of flaccid material adapted to fit over a male penis and having a length extending from the base of the penis to at least the corona of the penis;
   a second sleeve of flaccid material adapted to fit over the penis and having a length extending from the base of the penis to at least the corona of the penis; and
   at least one wall region disposed between said first sleeve and said second sleeve, said at least one wall region extending continuously along said length of said first sleeve and said length of said second sleeve, said at least one wall region coupled to said first sleeve and said second sleeve, said at least one wall region defining a void region along said length of said first sleeve and said length of said second sleeve.

2. A device as in claim 1, further comprising:
   a first elastic ring coupled to one axial end of at least one of said first sleeve and said second sleeve; and
   a second elastic ring coupled to another axial end of at least one of said first sleeve and said second sleeve.

3. A device as in claim 2, wherein said first elastic ring has a width dimension in the range of approximately 0.1 inches to approximately 0.3 inches and a height dimension in the range of approximately 0.1 inches to approximately 0.3 inches.

4. A device as in claim 1, wherein said void region has a width dimension in the range of approximately 0.25 inches to approximately 0.4 inches.

5. A device as in claim 1, further comprising indicia on at least one of said first sleeve and said at least one wall region, said indicia being located in diametric opposition to said void region.

6. A device as in claim 1, wherein said at least one wall region comprises a hollow and open-ended cylinder having a longitudinal split defining said void region.

7. A device as in claim 1, wherein said at least one wall region has a thickness dimension in the range of approximately 0.1 inches to approximately 0.25 inches.

8. A device as in claim 1, wherein said at least one wall region comprises a plurality of spaced-apart wall regions.

9. A device as in claim 1, wherein each of said wall regions is tapered at opposing longitudinal ends thereof.

10. A device as in claim 1, further comprising a closed end sheath coupled to an axial end of at least one of said first sleeve and said second sleeve.

11. A device providing erection assistance, comprising:
a first sleeve of flaccid material adapted to fit over a male penis and having a length extending from the base of the penis to at least the corona of the penis;
a second sleeve of flaccid material adapted to fit over the penis and having a length extending from the base of the penis to at least the corona of the penis;
at least one wall region disposed between said first sleeve and said second sleeve, said at least one wall region extending continuously along said length of said first sleeve and said length of said second sleeve, said at least one wall region coupled to said first sleeve and said second sleeve, said at least one wall region defining a void region along said length of said first sleeve and said length of said second sleeve; and
an elastic ring coupled to one axial end of at least one of said first sleeve and said second sleeve, said elastic ring having a width dimension in the range of approximately 0.1 inches to approximately 0.3 inches and a height dimension in the range of approximately 0.1 inches to approximately 0.3 inches.

12. A device as in claim 11, further comprising another elastic ring coupled to another axial end of at least one of said first sleeve and said second sleeve.

13. A device as in claim 11, wherein said void region has a width dimension in the range of approximately 0.25 inches to approximately 0.4 inches.

14. A device as in claim 11, further comprising indicia on at least one of said first sleeve and said at least one wall region, said indicia being located in diametric opposition to said void region.

15. A device as in claim 11, wherein said at least one wall region comprises a hollow and open-ended cylinder having a longitudinal split defining said void region.

16. A device as in claim 11, wherein said at least one wall region has a thickness dimension in the range of approximately 0.1 inches to approximately 0.25 inches.

17. A device as in claim 11, wherein said at least one wall region and said elastic ring comprise a solid material.

18. A device as in claim 11, wherein said at least one wall region comprises a plurality of spaced-apart wall regions.

19. A device as in claim 18, wherein each of said wall regions is tapered at opposing longitudinal ends thereof.

20. A device as in claim 11, further comprising a closed end sheath coupled to an axial end of at least one of said first sleeve and said second sleeve.

21. A device providing erection assistance, comprising:
an outer sleeve of flaccid material adapted to fit over a male penis and having a length extending from the base of the penis to the corona of the penis;
an inner sleeve of flaccid material adapted to fit over the penis and having a length extending from the base of the penis to the corona of the penis;
a plurality of spaced-apart wall regions captured between said outer sleeve and said inner sleeve, each of said wall regions extending continuously along said length of said outer sleeve and said length of said inner sleeve wherein a longitudinal spacing is defined between adjacent ones of said wall regions and wherein said longitudinal spacing is greatest between two adjacent ones of said wall regions to thereby define a void region, each of said wall regions coupled to said outer sleeve and said inner sleeve;
a first elastic ring coupled to one axial end of at least one of said outer sleeve and said inner sleeve, said first elastic ring having a width dimension in the range of approximately 0.1 inches to approximately 0.3 inches and a height dimension in the range of approximately 0.1 inches to approximately 0.3 inches;
a second elastic ring coupled to another axial end of at least one of said outer sleeve and said inner sleeve; and
indicia in diametric opposition to said void region, said indicia being placed on at least one of said outer sleeve and one of said wall regions.

22. A device as in claim 21, wherein said longitudinal spacing associated with said void region is in the range of approximately 0.25 inches to approximately 0.4 inches.

23. A device as in claim 21, wherein each of said wall regions has a thickness dimension spanning between said outer sleeve and said inner sleeve, said thickness dimension being in the range of approximately 0.1 inches to approximately 0.25 inches.

24. A device as in claim 21, wherein each of said wall regions is tapered at opposing longitudinal ends thereof.

25. A device as in claim 21, further comprising a closed end sheath coupled to said another axial end of at least one of said outer sleeve and said inner sleeve.

26. A device as in claim 21, wherein each of said wall regions and said first elastic ring comprise a solid material.

* * * * *

UNITED STATES PATENT AND TRADEMARK OFFICE
CERTIFICATE OF CORRECTION

PATENT NO.        : 9,295,579 B1
APPLICATION NO.   : 14/824650
DATED             : March 29, 2016
INVENTOR(S)       : Ronald G. Bublick and Linda L. Bublick Page 1 of 1

It is certified that error appears in the above-identified patent and that said Letters Patent is hereby corrected as shown below:

Title Page
All Applicants and Inventors state of residence should be "VA".

Signed and Sealed this
Twenty-first Day of June, 2016

Michelle K. Lee
*Director of the United States Patent and Trademark Office*